US00PP22899P2

(12) United States Plant Patent
Kivistik

(10) Patent No.: US PP22,899 P2
(45) Date of Patent: Jul. 31, 2012

(54) ***CLEMATIS* PLANT NAMED 'UNAI 009'**

(50) Latin Name: *Clematis jackmanii*
Varietal Denomination: UNAI 009

(76) Inventor: Aili Kivistik, Kose Parish (EE)

( * ) Notice: Subject to any disclaimer, the term of this patent is extended or adjusted under 35 U.S.C. 154(b) by 0 days.

(21) Appl. No.: 12/932,188

(22) Filed: Feb. 17, 2011

(51) Int. Cl.
*A01H 5/00* (2006.01)

(52) U.S. Cl. ..... Plt./228

(58) Field of Classification Search ..... Plt./228
See application file for complete search history.

*Primary Examiner* — Annette Para
(74) *Attorney, Agent, or Firm* — Cassandra Bright

(57) ABSTRACT

A new and distinct *Clematis* cultivar named 'UNAI 009' is disclosed, characterized by good resistance to normal diseases and pests of *Clematis*, continuous flowering from May through September, with flower buds continuously produced from the leaf axils. Plants are exceptionally compact and floriferous and produce flowers with tepals colored Violet with a Red-Purple central bar. The new cultivar is a *Clematis*, suitable for ornamental garden purposes.

2 Drawing Sheets

Latin name of the genus and species: *Clematis jackmanii.*
Variety denomination: 'UNAI 009'.

BACKGROUND OF THE INVENTION

The new cultivar is a product of a planned breeding program conducted by the inventor that began in 1978. In 1982 the inventor, Aili Kivistik a citizen of Estonia, organized a group of unnamed, unpatented *Clematis jackmanii* varieties for an open pollination breeding project. Seeds originating from this crossing were planted out, and the new variety was selected in 1985. Specific parents of the new variety are unknown, as the seed was bulk collected, without noting the variety collected from. All work was conducted at a non-commercial nursery in Roogoja, Estonia.

In 1987 the inventor first propagated 'UNAI 009' by vegetative cuttings at the same non-commercial nursery in Roogoja, Estonia. Subsequent generations have shown that the unique features of this cultivar are stable and reproduced true to type.

SUMMARY OF THE INVENTION

The cultivar 'UNAI 009' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'UNAI 009' These characteristics in combination distinguish 'UNAI 009' as a new and distinct *Clematis* cultivar:

1. Prolific flowering
2. Continuous flowering from May through September.
3. Flower buds produced continuously from the leaf axils.
4. Violet tepal coloration with center bar faintly Red-Purple.
5. Compact plant habit.

6. Durability of foliage to mechanical, disease and pest damage.

COMPARISON TO KNOWN VARIETIES

Plants of the new cultivar 'UNAI 009' are similar to known forms of *Clematis jackmanii* in most horticultural characteristics, however, plants of the new cultivar 'UNAI 009' produce flowers with a larger overall diameter than common forms of *Clematis jackmanii* known to the inventor. Additionally, plants of 'UNAI 009' flower continuously from May through September, whereas many known forms of *Clematis jackmanii* flower reliably 2 months only.

The new cultivar 'UNAI 009' can also be compared to the unpatented variety *Clematis* 'Perle d'Azure'. Plants are similar in most horticultural characteristics, however, plants of the new cultivar produces flowers with tepals that are more narrow, an overall flower diameter that is slightly larger, and different colored stamens. Additionally the new has an overall shorter, more compact plant habit.

BRIEF DESCRIPTION OF THE PHOTOGRAPHS

Figure 1:
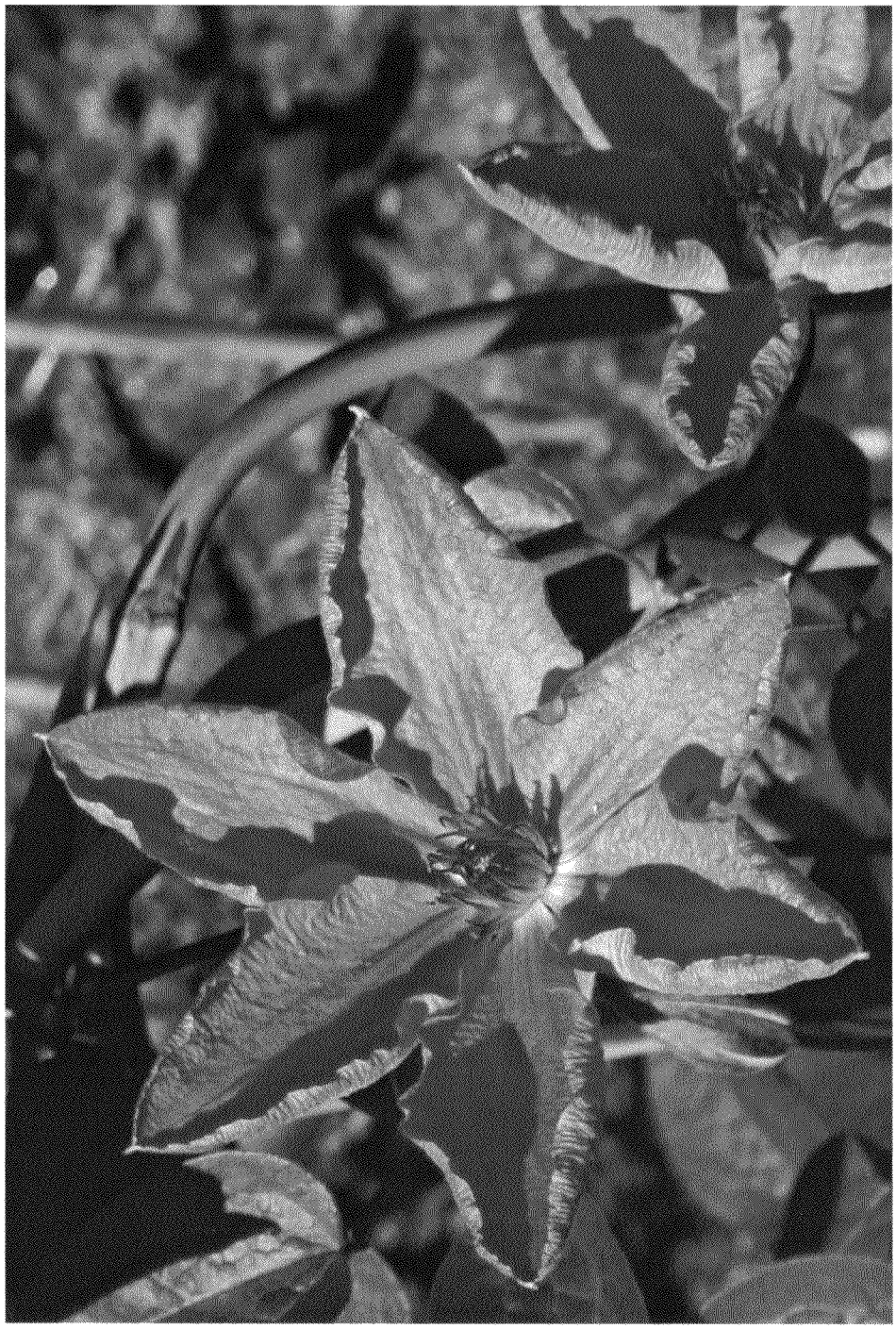

The accompanying photograph in FIG. 1 illustrates in full color a close up of typical foliage and the reverse side of flowers of 'UNAI 009'.

Figure 2:
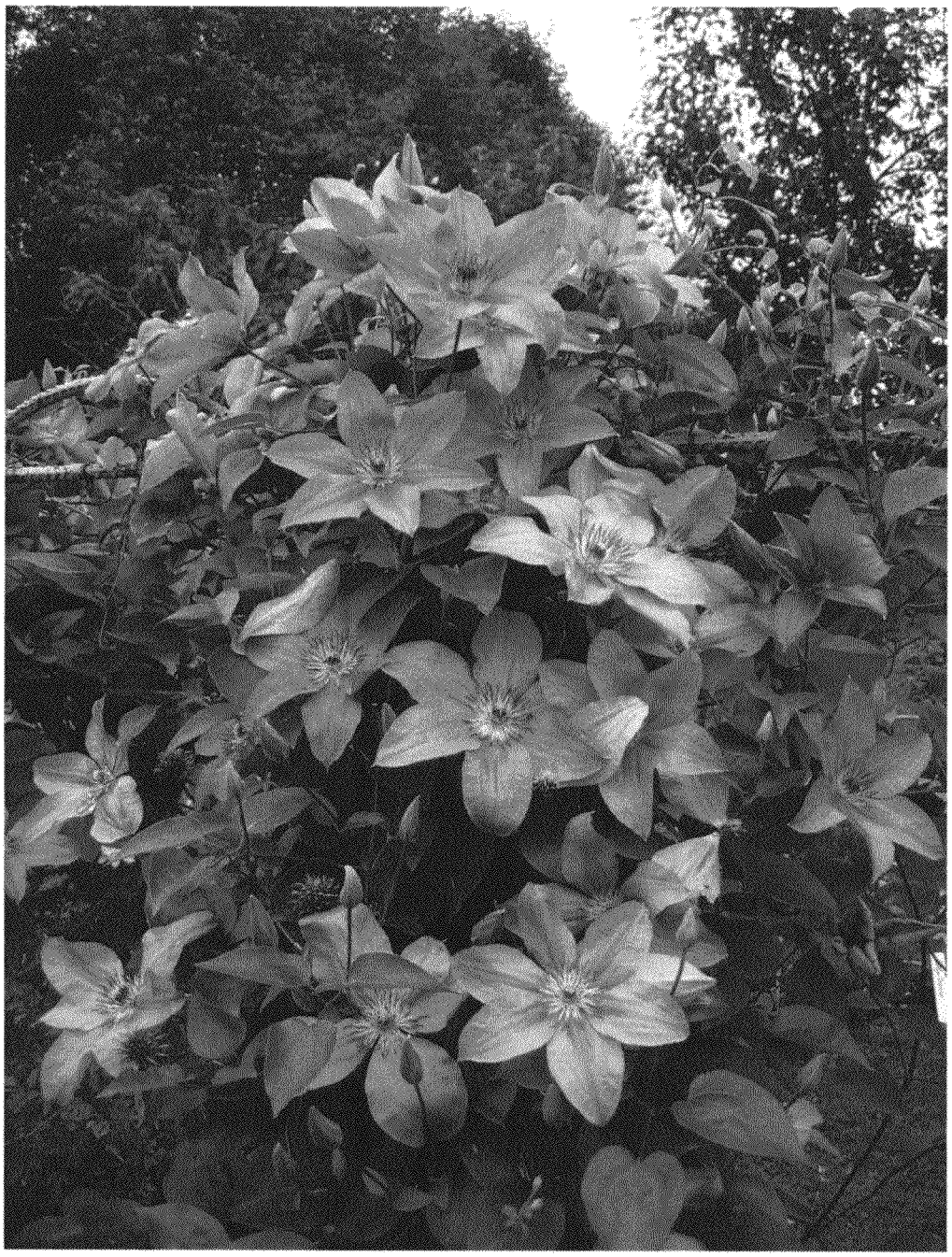

FIG. 2 shows a close up of a typical flower of 'UNAI 009' grown outdoors in Estonia.

The plant is approximately one year old. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001, except where general terms of ordinary dictionary significance are used. The following observations and measurements describe 'UNAI 009' plants grown outdoors in Roogoja, Estonia. Plants are approximately 1 year old, in a 5 liter nursery container. The growing conditions are outdoors and unshaded. Temperatures ranged from approximately −2° C. to 20° C. at night to 5° C. to 35° C. during the day. Measurements and numerical values represent averages of typical plant types.

Botanical classification: *Clematis jackmanii* 'UNAI 009'.

PROPAGATION

Time to rooting:

*Initiation*.—Approximately 40 days in the Summer at approximately 25° C.

*Rooted cuttings production*.—Approximately 40 days in the Summer at approximately 25° C.

Root description: Fine, fibrous.

PLANT

Growth habit: Climbing vine.

Height: Approximately 200 cm, measured from the soil line of the pot after approximately 1 year.

Plant spread: Approximately 100 cm.

Growth rate: Rapid. During active growing season in Spring, approximately 80 cm per month.

Branching characteristics: Very well branched, one main branch with at least 5 to 6 lateral branches.

Length of main stem: Approximately 200 cm.

Diameter of main stem: Approximately 0.2 to 0.5 cm.

Main stem color: Near RHS Brown 200B.

Main stem texture: Glabrous.

Internode length: Varies from 10 to 15 cm.

Strength: Strong, flexible, semi-woody.

FOLIAGE

Leaf:

*Type*.—Ternate leaves arranged opposite. Some leaves simple opposite.

*Leaves per lateral branch*.—Approximately 60 leaflets.

*Average length*.—Approximately 5 cm.

*Average width*.—Approximately 3 cm.

*Shape of blade*.—Heart shaped.

*Apex*.—Acute.

*Base*.—Cordate.

*Attachment*.—Petioled.

*Margin*.—Entire.

*Texture of top surface*.—Smooth.

*Texture of bottom surface*.—Smooth.

*Leaf internode length*.—Approximately 2 cm.

*Resistance to stress and breakage*.—Very resistant to environmental and mechanical stress.

*Color*.—Young foliage upper side: Near RHS Green 136C. Young foliage under side: Near RHS Green 137D. Mature foliage upper side: Near RHS Green 136A. Mature foliage under side: Near RHS Green 137C.

*Venation*.—Type: Pinnate. Venation color upper side: Near RHS Green 136A. Venation color under side: Near RHS Green 137C.

*Petiole*.—Average Length: Approximately 6 cm. Color: Near RHS Green 136A. Diameter: Approximately 0.2 cm. Texture: Glabrous. Angle to stem: 90° to stem.

Tendrils not present.

FLOWER

Bloom period:

*Natural season*.—Continuously from approximately May through September.

Inflorescence type and habit: Single, rotate, axillary; flowers facing outward.

Flower longevity on plant: Approximately 5 days, after fully opened. Self-cleaning.

Quantity of flowers: Very free, continuous flowering. Mature plants have at least 40 open flowers at one time during the flowering season.

Inflorescence size:

*Diameter*.—Approximately 15 to 20 cm.

*Depth*.—Approximately 1 cm.

Corolla:

*Tepal arrangement*.—Single whorl. Overlapping.

*Quantity*.—Approximately 6 per flower.

*Size*.—Length: Approximately 8 cm. Width: Approximately 4 cm.

*Margin*.—Entire.

*Apex*.—Acute.

*Base*.—Truncate.

*Aspect*.—Moderately concave. Margins slightly up turned.

*Texture*.—Smooth, velvety.

Color:

*Tepals*.—When opening: Upper surface: Near RHS Violet-Blue 91A, center bar near Red-Purple 71A. Lower surface: Near RHS Violet 88C.

*Fully opened*.—Upper surface: Near RHS Violet-Blue 91A, faint center bar near Red-Purple 72B. Lower surface: Near RHS Purple 79C.

*Ageing*.—Upper Surface: Near RHS Violet-Blue 94D, center bar either completely gone, or very faint Purple 77C. Lower surface: Near RHS Violet-Blue 94D.

Bud:

*Shape*.—Conical.

*Length*.—Approximately 2 cm.

*Diameter*.—Approximately 1 cm.

*Color*.—Mainly Near RHS Greyed-Green 192D.

Pedicels:

*Length*.—Approximately 0.5 cm.

*Width*.—Approximately 0.3 cm.

*Angle*.—Average 45°.

*Strength*.—Moderate.

*Color*.—Near RHS Green 138A.

Fragrance: None.

REPRODUCTIVE ORGANS

Stamens:

*Number*.—Approximately 60 per flower.

*Anther length*.—0.4 cm.

*Anther color*.—Near RHS Greyed-Purple 187B.

*Anther shape*.—Oblong.

*Pollen*.—Pollen not observed to date.

*Filament length*.—Approximately 0.5 cm.

*Filament aspect*.—Straight to slightly outwardly curved.

*Filament color*.—Near RHS Purple 80D.

Pistil:

*Number*.—Approximately 30 per flower.

*Length*.—Approximately 2 cm.

*Style color*.—Near RHS White 155B at base, upper 75% near Purple N79C.

*Style length*.—Approximately 0.5 cm.

*Stigma*.—Shape: Linear. Color: Near RHS Yellow 11D.

OTHER CHARACTERISTICS

Seeds: Per flower, typically 30 round seeds, approximately 0.15 diameter. Colored near RHS Green 137B.

Disease/pest resistance: Very good resistance to pathogens and pests common to *Clematis* has been observed.

Temperature tolerance: Observed to tolerate temperatures from approximately −5° C. to at least 35° C.

What is claimed is:

1. A new and distinct cultivar of *Clematis* plant named 'UNAI 009' as herein illustrated and described.

* * * * *